United States Patent [19]

Niedrach et al.

[11] Patent Number: 4,990,855
[45] Date of Patent: Feb. 5, 1991

[54] CONDUCTIVITY PROBE FOR USE IN THE PRESENCE OF HIGH INTENSITY NUCLEAR RADIATION

[75] Inventors: Leonard W. Niedrach; Dale F. Taylor, both of Schenectady, N.Y.

[73] Assignee: General Electric Company, Schenectady, N.Y.

[21] Appl. No.: 368,680

[22] Filed: Jun. 19, 1989

[51] Int. Cl.$^5$ ............................................. G01N 27/26
[52] U.S. Cl. ................................... 324/449; 324/71.3; 324/446; 324/464; 204/431; 376/256
[58] Field of Search ................. 204/431, 432; 376/256, 376/245, 249; 324/71.3, 449, 446, 464

[56] References Cited

U.S. PATENT DOCUMENTS

| | | | |
|---|---|---|---|
| 3,649,473 | 3/1972 | Holden | 376/256 |
| 4,507,521 | 3/1985 | Goellner | 174/151 |
| 4,567,013 | 1/1986 | Smith | 376/256 |
| 4,626,786 | 12/1986 | Bodecker et al. | 324/449 |
| 4,769,607 | 9/1988 | Bauman et al. | 324/446 |
| 4,948,492 | 8/1990 | Niedrach | 376/256 |

FOREIGN PATENT DOCUMENTS

| | | | |
|---|---|---|---|
| 2829465 | 1/1979 | Fed. Rep. of Germany | 376/256 |
| 3221625 | 1/1983 | Fed. Rep. of Germany | 376/249 |

OTHER PUBLICATIONS

Ceramic to Metal Sealing, L. Reed, Electronic Ceramics, Special Publication No. 3, American Ceramic Society, pp. 34–42, CA 1970.
Ceramic to Metal Bonding, C. I. Helges, Boston Technical Publishers, Cambridge, Mass., 1968, pp. 8–21.
Materials and Techniques for Electron Tubes, W. H. Kohl, Reinhold Publishing Corp., N.Y., N.Y., 1960, pp. 488–493.

Primary Examiner—Reinhard J. Eisenzopf
Assistant Examiner—Jose M. Solis
Attorney, Agent, or Firm—James E. McGinness; James C. Davis, Jr.; James Magee, Jr.

[57] ABSTRACT

A conductivity probe able to withstand high water temperatures and pressures, and intense nuclear radiation is suitable for use within the core of the nuclear reactor. The probe is made with a ceramic insulator, such as sapphire, and a central electrode that is mounted on the insulator. A sleeve that supports the insulator and the central electrode is made from metals having a coefficient of thermal expansion compatible with the coefficient of thermal expansion of the insulator, such as Kovar. The central electrode and sleeve are bonded to the insulator by a brazed compressive seal that protects an internal conductor in the probe from intrusion of the reactor water. A counter electrode made from a corrosion resistant metal, such as Kovar, is attached to the sleeve so that it extends over the central electrode a fixed, spaced distance. A positioning and signal transfer arrangement operatively supports the sleeve and conveys electrical signals to and from the two electrodes.

9 Claims, 3 Drawing Sheets

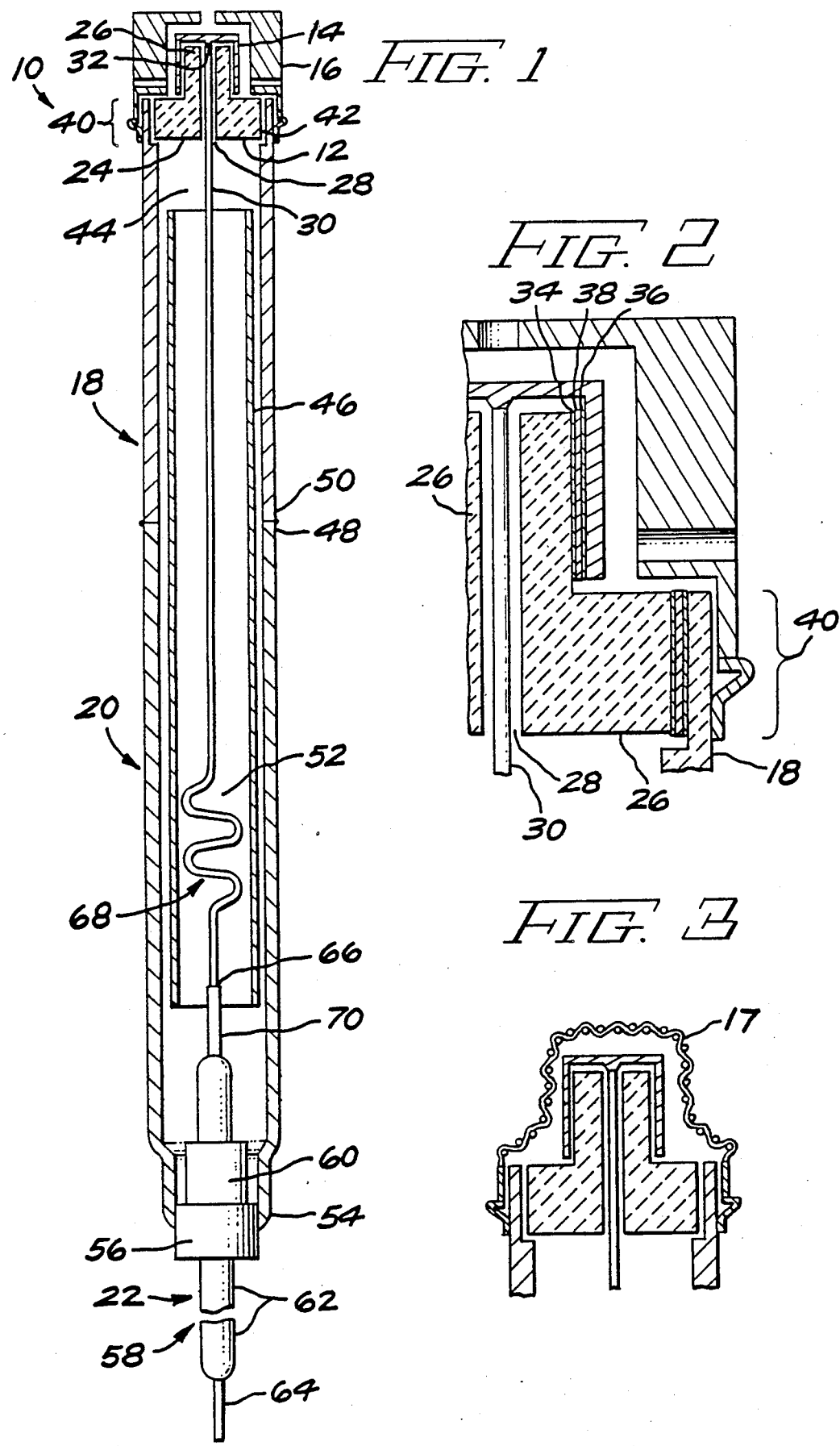

CONDUCTIVITY PROBE FOR USE IN THE PRESENCE OF HIGH INTENSITY NUCLEAR RADIATION

BACKGROUND OF THE INVENTION

The nuclear power industry long has been engaged in a multitude of studies and investigations seeking improvement in the stamina and reliability of the materials and components forming a reactor-based power system. One such investigation has been concerned with intergranular stress corrosion cracking which heretofore principally has been manifested in the water recirculation piping systems external to the radiation intense reactor core regions of nuclear facilities. Typically, the piping architecture of these external systems is formed of a stainless steel material.

Generally, the studies referred to above have determined that three factors must occur in coincidence to create conditions that promote intergranular stress corrosion cracking. One factor is a sensitization of the metal such as stainless steel, for example, by chromium depletion at grain boundaries. Chromium depletion at grain boundaries may be caused by heat treatment in the course of normal processing of the metal or by welding and the like procedures. A second factor is the presence of tensile stress in the material. A third factor is the oxygenated normal water chemistry environment typically present in a boiling water reactor. This latter environment is occasioned by any of a variety of oxidizing and corrosive species contributed by impurities in reactor coolant water. Corrosive species are generally impurity ions such as chlorides or sulfates. Therefore, monitoring of the corrosive species would be helpful in the study and control of intergranular stress corrosion cracking.

Electrical conductivity probes are used in liquids having at least a slight degree of electrical conductivity and are able to measure increases or decreases in that conductivity. A voltage is applied between separate electrodes immersed in the fluid. Small changes in current are then detected between the electrodes, as the concentration of conducting species changes. The electrodes must be well insulated from one another and arranged to provide a conducting path between them of fixed dimensions with paths for stray leakage currents minimized. As the concentration of corrosive species in the reactor water of a boiling water nuclear reactor increases, the conductivity of the water will increase. Therefore, conductivity probes measuring increases in the conductivity of reactor water can be used to detect increases in the concentration of corrosive species in that water.

While the conductivity probe can measure the conductivity of the water, certain parts of the conductivity probe must be insulatively sealed from intrusion of the water. An internal conductor and the connection between the conductor and an electrode in the probe must be sealed and protected from the reactor water to prevent electrical interference, shorting and corrosion of the conductor.

Conductivity probes developed for use in high-pressure and high temperature liquid environments have been configured with combinations of metal housings and ceramic insulators combined with mechanical interference or washer type seals made of polymeric or soft metallic materials. These structures have performed adequately in the more benign and essentially radiation free environments of, for example, recirculation piping in nuclear reactors.

Over the recent past, investigators have sought to expand the conductivity probe monitoring procedures to the severe environment of the fluid in the vicinity of the reactor core itself for the purpose of studying and quantifying the effect of corrosive species on stress corrosion cracking. Within the reactor core, conductivity probes can be mounted in specially designed small cross section tubing. Such tubing is located among the fuel elements in the reactor core, and is used to house various monitoring devices such as neutron detectors. As a result, these tubes are known as local power-range monitor tubes.

Thus, the conductivity probes are located in the severe environment of the fluid in the reactor core having a typical high temperature of 274° C., pressure of 1,000 psi, and radiation of $10^9$ rads per hour gamma and $10^{13}$ rads per hour neutron. Conductivity probe structures of earlier designs are completely inadequate for this reactor core environment, both from a material standpoint, and with respect to the critical need to prevent leakage of radioactive materials to the ambient environment of the reactor. For example, the polymeric seals used in most conductivity probes cannot withstand intense radiation with the result being failure of the probe and leakage of radioactive materials.

BRIEF SUMMARY OF THE INVENTION

A conductivity probe able to withstand the corrosion, water pressure and intense nuclear radiation within a reactor core of a nuclear power facility is provided in this invention. The conductivity probe also has a compact size so that it will fit within the small cross section of local power-range monitor tubes within the reactor core.

The conductivity probe is a sensor comprised of a central electrode mounted to form a brazed compressive seal on an insulator. The brazed compressive seal is able to withstand high intensity nuclear radiation and prevents the high pressure reactor water from leaking into the probe. The conductor carrying current to the central electrode is protected from electrical interference, shorting and corrosive attack by the reactor water. This is accomplished by forming the insulator to have a base region with an exterior attachment surface configured to form a tight-fitting seal in a sleeve that supports the sensor. The insulator has a post integrally formed and extending from the base, the post having an exterior attachment surface configured to form a tight fitting seal with an electrode to be placed over the post. The post and base are further configured to insulatively separate the sleeve from the central electrode on the post.

The insulator is made from a material that is resistant to corrosive attack from nuclear reactor water, able to withstand high-intensity nuclear radiation and is electrically non-conductive. A preferred material with these properties is single crystalline alumina also known as sapphire. A channel extends through the post and base of the insulator so that a conductor can be passed in an insulated manner through the insulator.

The central electrode is made from a material having a coefficient of thermal expansion compatible with the insulator, and resistant to corrosion from reactor water. A preferred material is KOVAR, an alloy typically consisting of by weight percent about 53.8 percent iron, about 29 percent nickel, about 17 percent cobalt and about 0.2 percent manganese. The central electrode has a concave interior surface configured to form a tight-fitting compressive seal on the post.

A sleeve for supporting the sensor is made from a metal having a coefficient of thermal expansion compatible with the insulator and resistant to corrosive attack from reactor water. In a preferred embodiment, the sleeve is made from Kovar. The sleeve has an acceptance portion for intimately sealed braze connection with the base of the insulator. An internal channel extends through the sleeve along its lengthwise extent.

The acceptance portion of the sleeve, the internal surface of the central electrode, and the external attachment surfaces of the base region and post on the insulator have metallized coatings applied to them for acceptance of a braze bond. The central electrode is brazed onto the post and the acceptance portion of the sleeve is brazed onto the insulator base forming brazed compressive seals therebetween. Such brazes, materials and configuration of each component in the structure of this invention, coordinate to form compressive seals able to withstand the rigorous environment of a nuclear reactor core.

A conductor extending through the channel in the insulator is connected in electrical contact with the interior surface of the central electrode.

A counter-electrode is made from a metal resistive to corrosion in reactor water such as Kovar or platinum. The counter-electrode is attached with an electrical current conducting bond to the sleeve and extends over the central electrode at a spaced, fixed distance. The counter-electrode contains a plurality of openings to permit a continuous exchange of reactor water between the central electrode and the counter-electrode.

A positioning and signal transfer arrangement is provided for operatively supporting the sleeve arrangement and for conveying electrical signals to and from the central electrode and the counter-electrode by way of the sleeve and the conductor.

BRIEF DESCRIPTION OF THE DRAWINGS

The following figures are provided with accompanying numerals to further show the conductivity probe of this invention.

FIG. 1: is a cross-section of the conductivity probe of this invention.

FIG. 2: is, an enlarged cross-section of FIG. 1, specifically showing the brazed connections.

FIG. 3: shows the cross-section of another embodiment of the present invention.

DETAILED DESCRIPTION OF THE INVENTION

Figure 4:
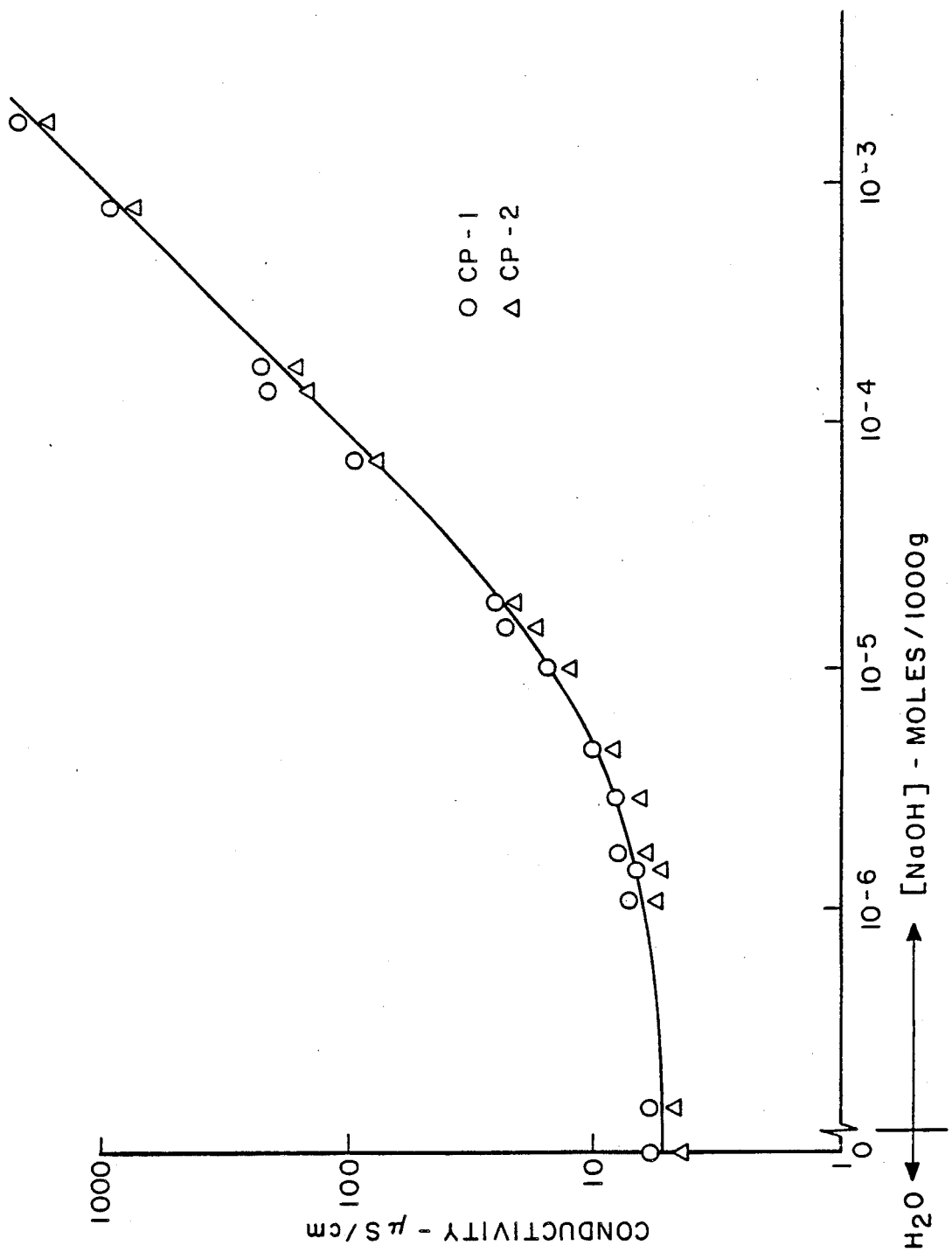
FIG. 4: is a graphical presentation of the conductivity values measured using conductivity probes of this invention immersed in water having a varied concentration of sodium hydroxide.

While having utility in a broad variety of industrial monitoring functions, the conductivity probe of the instant invention finds particular utility operating under the rigorous environment of the reactor core of a nuclear power facility. No elastomeric seals or polymeric components are present in the structure. Instead, ceramic and metallic components are bonded with brazed compressive seals to protect the internal parts of the sensor.

Referring to FIG. 1, the structure of the conductivity probe, according to the invention, is represented in general at 10 in sectional fashion. Device 10 has a generally cylindrical structure comprised of six principal components, including a cylindrically-shaped insulator 12, a cylindrically-shaped central electrode 14, a cylindrical counter-electrode 16, and a positioning and signal transfer arrangement which includes; a sleeve 18, an elongate cylindrical transition component or piece 20, and a cable assembly or connector 22.

Conductivity probe 10 is structured to withstand the duress imposed by radiation, high temperatures and high fluid pressure, while also achieving a highly reliable seal to avoid the incursion of reactor coolant water through the probe and ultimately to the outside environment. The insulator 12, in its preferred embodiment, is formed of sapphire, which is a single crystalline form of alumina. The sapphire material provides electrical insulation and, by virtue of its single crystalline structure, is highly resistant to attack from the water the probe is immersed in. Single crystalline sapphire has no grain boundaries so there is no intergranular penetration into the material, even though there will be some general corrosion attack. Other insulator materials will occur to those art skilled, for example, high purity alumina or ruby.

Insulator 12 is formed having a cylindrical base region 24, and an integrally formed smaller diameter cylindrical post 26 extending from the base. A cylindrical bore or continuous access channel 28 extends through the base and post. Channel 28 serves to provide access for an electrically conductive transmission line or conductor wire 30, which conductor can be formed of Kovar and flattened at its end position 32 in disk-shaped fashion.

A central electrode 14 made from a corrosion resistant material having a coefficient of thermal expansion similar to the insulator, such as Kovar or platinum, is cylindrically shaped with one closed end to form a tight fitting seal over post 26. Optionally, a coating of platinum black can be applied to a Kovar central electrode to improve its performance. Platinum black is a finely divided platinum deposit that increases the surface area on the deposited surface. The outside diameter of the post and the inside diameter of the central electrode are machined to have a difference in diameter of about 0.004 inch to provide the tight fit.

To achieve a sealed union of high integrity between the concave internal surface of the central electrode 14 and the outer surface of post 26, a seal of the type known as the sintered metal powder process is made on the post. A paint containing metal powders such as molybdenum or tungsten, and sometimes containing glass forming or modifying oxides such as $SiO_2$ or $MnO$ is applied to the post and fired in a wet hydrogen atmosphere having dew points in the $-5°$ C. to $+20°$ C. range to sinter the coating. A glassy phase having a mixture of glass and crystalline phases forms a tightly adherent seal on the ceramic insulator. Further explanation of the sintered metal powder process can be found in "Material and Techniques for Electron Tubes" by W. H. Kohl, Reinhold Publishing Corp., N.Y. 1960, pp. 488–493, which is incorporated by reference herein.

The fired surface is inspected and the thus-metallized region is nickel-plated and heated to sinter the metallized layer and nickel plating. The sintered surface is then inspected and silver plated. The inspections are performed to assure the continuity of the platings. This surface treatment 34 prepares the insulator for acceptance of a silver braze bond.

The machined central electrode 14 is prepared by cleaning and inspecting it, followed by a post-machine annealing procedure. The electrode inner surface is then nickel plated, sintered to improve the plating bond, and inspected. A second nickel plate and sintering procedure is carried out, followed by inspection. Optionally, the electrode is silver-plated on its inner surface and the silver plating is sintered and inspected. A second silver-plating is applied, sintered and inspected. If the central electrode is not brazed to the insulator post at the time the metallized layers are applied, the optional silver plating provides protection for the nickel coatings. This surface treatment 36 prepares the central electrode for acceptance of a silver braze bond.

In the assembly of this sealing arrangement, the conductor 30 is spot welded to the inside surface of the central electrode 14. Additionally, the central electrode 14 is sealably attached to the surface of post 26 by silver brazing 38, forming a reliable compressive seal. Conductor 30 extends from the central electrode through the channel in the insulator. This metallized coating and brazing is shown in the enlarged cross-section of FIG. 2 and should be understood to be present in the structures shown in FIGS. 1 and 3, though it is not specifically shown in FIGS. 1 and 3.

Returning to FIG. 1, the lower outer cylindrical surface portion of base region 24 of the insulator 12 is a surface attachment region, the extent of which is represented by bracket 40. Referring to FIG. 2, this region also is metallized in the same manner as the surface of post 26. The cylindrical sleeve 18 is made from a metal resistive to corrosion and having a thermal coefficient of expansion similar to the insulator. In a preferred embodiment, the sleeve is formed of Kovar. The internal diameter of the sleeve 18 is offset, for example, by counterboring at 42 to provide an acceptance portion suited for receiving and being attached to the surface attachment region 40 of base region 24 of insulator 12 for forming an intimate seal thereat. The outside diameter of the base region and the inside diameter of the acceptance portion in the sleeve are machined to have a difference in diameter of about 0.004 inch to provide a tight fit.

The initially-produced cylinder of Kovar for sleeve 18 is prepared by cleaning and inspecting it, following which a post machine annealing procedure is carried out. Following this annealing procedure, the component is nickel-plated, sintered, and inspected. A second nickel plating and sintering procedure then is carried out, followed by a next inspection. Generally, the thus prepared component is stored in sealed plastic packaging until it is utilized. An intimate compressive seal between the surface attachment region 40 of insulator 12 and the acceptance portion 42 of sleeve 18 is provided by silver brazing. This arrangement then completes a highly secure second seal for the conductivity probe 10 as is required in view of the intended use thereof within the environment of a nuclear reactor core.

The hollow interior 44 of cylindrical sleeve 18 provides an internal channel through which the conductor 30 may pass. To assure that the conductor 30 is insulated from the internal surfaces of sleeve 18, an alumina tube 46 is inserted within channel 44. Annular ceramic tube 46 provides such insulation while remaining immune from the temperatures encountered with the intended use of device 10.

Counter-electrode 16 is made from a metal resistant to corrosion in a nuclear reactor core, such as platinum or Kovar. The counter-electrode is configured to mount on sleeve 18 so that it extends over the central electrode 14 a fixed spaced distance. An electrical current conducting bond, such as a tungsten inert gas weld, is made to attach the counter-electrode to the sleeve. A plurality of openings in the counter-electrode permits a continuous exchange of reactor-core water to fill the gap between the two electrodes. Optionally, a coating of Platinum-black may be deposited on a Kovar counter-electrode as on the central electrode.

Referring now to FIG. 3, a second embodiment of the present invention is shown wherein a wire mesh screen 17 is used to form the counter electrode extending a fixed, spaced distance over the central electrode. The wire mesh is made from a metal resistive to corrosion in the nuclear reactor core, such as platinum or Kovar. The wire mesh permits a continuous exchange of reactor-core water to fill the gap between the two electrodes.

Referring back to FIG. 1, Kovar sleeve 18 is supported by attachment to the cylindrical transition component 20 that may be formed of a type 304 stainless steel. The transition piece 20 is of corresponding diametric extent as sleeve 18 and is attached at its transition end 48 to the corresponding attachment surface 50 thereof, utilizing a tungsten inert gas weld, as applied, for example, by a tube welder. The hollow interior 52 of transition tube 20 provides an internal channel representing a continuation of channel 44 of sleeve 18. Alumina tube 46 is seen to extend continuously thereinto. The lower end of transition tube 20 is formed in neck down fashion to provide a sealing end 54. End 54 is welded by the noted tungsten inert gas welding technique to the cylindrical stainless steel collar 56 of a cable connector assembly represented generally at 58 and which is shown having a ceramic support component 60 through which a mineral insulated cable 62 extends. Cable 62 has a stainless steel outer shell having the noted mineral insulation provided as alumina insulating the centrally disposed conducting cable 64 within the cable 62. The mineral insulated cable 62 extends outwardly to the ambient environment from the reactor core region in the application of interest. To provide an electric circuit completing connection with the lead 70, Kovar conductor 30 is spotwelded thereto at 66. To facilitate this attachment, a spring winding is formed in conductor 30 as represented in general at 68. Cable assembly 58 is marketed, for example, by Reutor-Stokes, a division of General Electric Company, Twinsburg, Ohio.

EXAMPLES

Two conductivity probes, CP-1 and CP-2, corresponding to the probes in FIGS. 1 and 3 respectively, were tested during more than three months of continuous operation. For this purpose, the two probes were inserted in a one-liter autoclave maintained at 285° C. at a pressure of 1200 psi. High purity, demineralized water was fed to the autoclave at a constant nominal rate of 30 milliliters per minute. During various phases of the work, the feed water was equilibrated with 10 percent hydrogen, or 0.5% oxygen to produce nominal water concentrations in the autoclave of 160 parts per billion (ppb) hydrogen, or 200 ppb oxygen, respectively.

In order to introduce variations in conductivity, a sidestream of sodium hydroxide (NaOH) was injected into the main feedwater stream using a metering pump capable of injection rates of 0.2 to 2.6 milliliters per minute.

The monitoring instrument employed to make measurements with the two probes was a Leeds and Northrup Multi-Range Conductivity Analyzer, Model 7076-1. For this purpose, and because temperature compensation was not required, a fixed resistance was substituted for the normal temperature compensating thermistor per Leeds and Northrup Instruction manual 277050F, 1985. The Leeds and Northrup analyzer furnishes a 320 Hertz, square wave signal and when employed for measurements near ambient temperature can provide a digital readout in conductivity units of microsiemens per centimeter ($\mu$S/cm), as well as a recorder signal. Because the measurements were made at the elevated temperature of 285° C. which is outside the normal operating range, the built-in controls for range adjustment of the digital readout did not lend themselves to such direct readout. Therefore, the digital readout of the instrument was converted to conductance using a calibration curve prepared independently by substituting standard resistances of known value for the conductivity cell; this is based upon the relationship $R = 1/\sigma$, where R is resistance and $\sigma$ is conductance. In order to convert such conductance values to specific conductivities—the conductance across a 1 cm gap having a cross-sectional area of 1 cm$^2$—the conductance values must, in turn, be multiplied by a geometric constant known as the cell constant that characterizes the fixed space between the electrodes. The cell constants for the two conductivity probes were determined by immersion in 0.01 molal potassium chloride at room temperature. By briefly pulling a vacuum on the system with the sensor immersed, it was possible to assure that no bubbles were left within the electrolyte gap between electrodes to invalidate the calibration. A general radio impedence bridge, model 1650A, operating at 1 kilohertz, was used to measure cell constants of 0.155 cm$^{-1}$ and 0.129 cm$^{-1}$ for probes CP-1 and CP-2, respectively. The same procedure yielded a value of 0.100 cm$^{-1}$ for a commercial sensor having a stated cell constant of 0.100 cm$^{-1}$.

Demonstration of the two probes was made by determining their responses to changes in the conductivity of water in the autoclave. The water conductivity was varied by the injection of sodium hydroxide into the high purity feed water for the autoclave. Such data, summarized in Table I, were derived from the instrumental readings using the calibration procedure and cell constants as outlined above.

Figure 5:
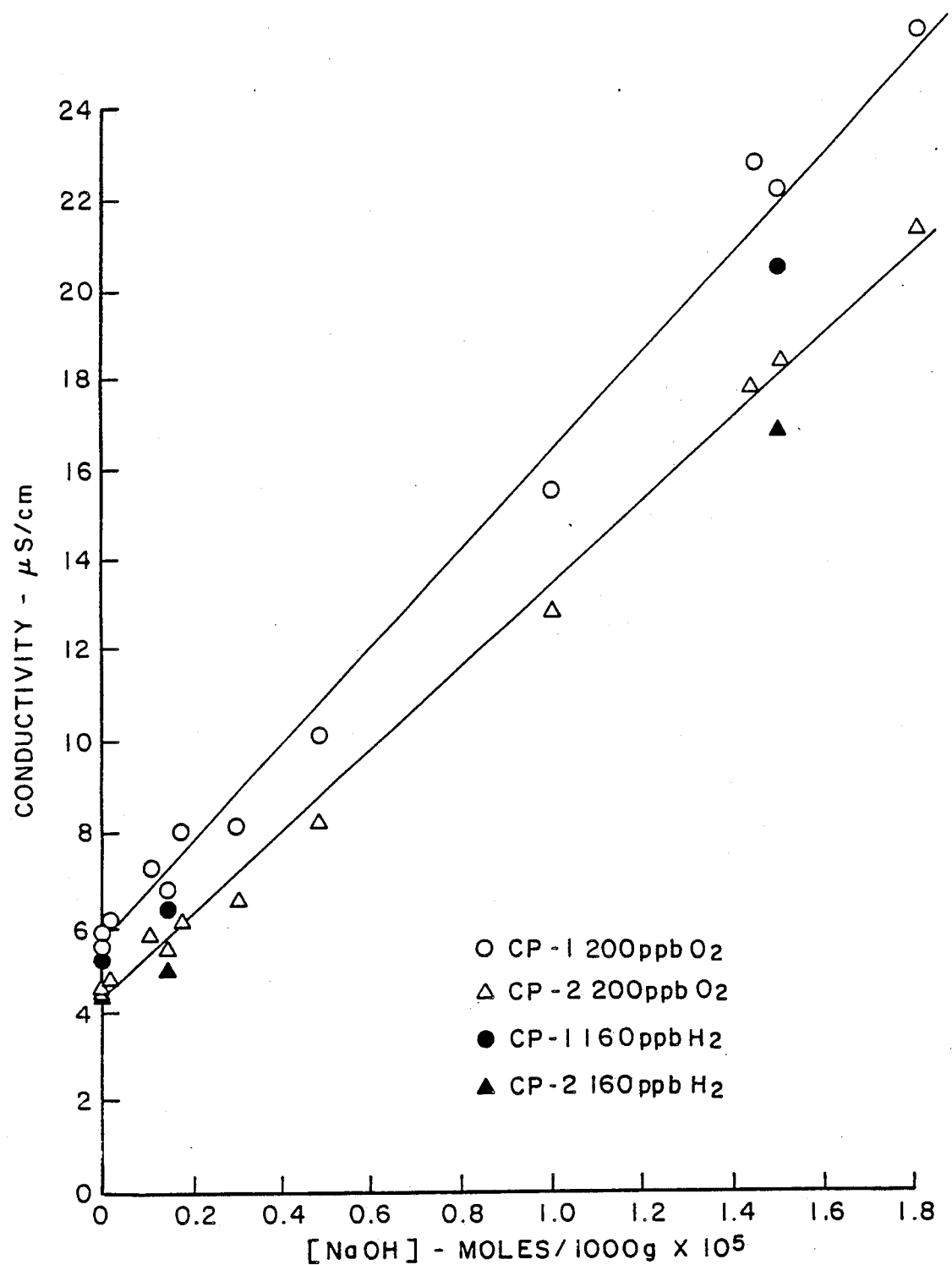
FIG. 5: is another graphical presentation of the conductivity values measured by conductivity probes of this invention immersed in water having a varied concentration of sodium hydroxide.

In FIGS. 4 and 5, the measured conductivity values as shown on the ordinate are plotted against the solute concentration as shown on the abscissa. The solid curve in FIG. 4 fits the equation, $$K = 5.2 + 1.05 \times 10^{-6} C$$

where K is the specific conductivity in $\mu$S cm$^{-1}$ and C is the molal concentration of the sodium hydroxide. The good linear correlation of the data over the full concentration range is to be expected theoretically. As the sodium hydroxide concentration approaches zero, the conductivity approaches a value consistent with the documented values for pure water of 2.9 to 4.2 $\mu$S/cm. The fact that the observed values are somewhat higher than the reported values for pure water, undoubtedly reflects the presence of corrosion products in the water as evidenced further by the fact that the ambient temperature conductivity of the effluent water from the autoclave was observed to be higher than that of the influent, 0.4 vs. 0.07 $\mu$S/cm, respectively.

As can be seen from the last six measurements in Table 1, examples 17 through 22, detectable differences are evident between normal water chemistry and hydrogen water chemistry conditions. Such changes are associated with the formation of chromic acid in the water, under normal water chemistry conditions, and the formation of iron and nickel hydroxides under hydrogen water conditions. This is further demonstrated in FIG. 5, which compares conductivity measurements for probes CP-1 and CP-2. The solid data points represent the 160 ppb hydrogen water chemistry and are consistently lower than the 200 ppb oxygen water chemistry data points represented by the open data points. The abscissa in FIG. 5 contains a break which has been employed to show the transition from high purity water on the left of the break and the beginning of the addition of small amounts of sodium hydroxide to the right of the break.

TABLE I

Summary of Conductivity Probe Test Conditions and Measured Conductivities

| Example | Type Water | NaOH Concentration moles/1000 g | Conductivities - $\mu$s/cm Probe CP-1 | Probe CP-2 |
|---|---|---|---|---|
| 1 | 200 ppb O$_2$ | 1.63 × 10$^{-4}$ | 248 | 161 |
| 2 | " | 7.9 × 10$^{-4}$ | 930 | 729 |
| 3 | " | 1.80 × 10$^{-3}$ | 2294 | 1670 |
| 4 | " | 1.63 × 10$^{-4}$ | 232 | 155 |
| 5 | " | 1.35 × 10$^{-4}$ | 217 | 148 |
| 6 | " | 7.11 × 10$^{-5}$ | 93 | 77 |
| 7 | " | 1.44 × 10$^{-5}$ | 22.9 | 17.8 |
| 8 | " | — | 5.89 | 4.52 |
| 9 | " | 1.76 × 10$^{-6}$ | 8.06 | 6.19 |
| 10 | " | 1.08 × 10$^{-6}$ | 7.21 | 5.74 |
| 11 | " | 1.50 × 10$^{-7}$ | 6.04 | 4.71 |
| 12 | " | 1.81 × 10$^{-5}$ | 25.7 | 21.3 |
| 13 | " | 4.76 × 10$^{-6}$ | 10.1 | 8.19 |
| 14 | " | 1.50 × 10$^{-6}$ | 6.67 | 5.48 |
| 15 | " | 9.9 × 10$^{-6}$ | 15.5 | 12.9 |
| 16 | " | 2.98 × 10$^{-6}$ | 8.06 | 6.45 |
| 17 | " | 1.50 × 10$^{-6}$ | 6.59 | 5.42 |
| 18 | 160 ppb H$_2$ | 1.50 × 10$^{-6}$ | 6.28 | 4.97 |

TABLE I-continued

| | Summary of Conductivity Probe Test Conditions and Measured Conductivities | | | |
|---|---|---|---|---|
| | Type | NaOH Concentration | Conductivities - $\mu s/cm$ | |
| Example | Water | moles/1000 g | Probe CP-1 | Probe CP-2 |
| 19 | 200 ppb $O_2$ | $1.50 \times 10^{-5}$ | 22.2 | 18.4 |
| 20 | 160 ppb $H_2$ | $1.50 \times 10^{-5}$ | 20.5 | 16.8 |
| 21 | 200 ppb $O_2$ | — | 5.42 | 4.64 |
| 22 | 160 ppb $H_2$ | — | 5.19 | 4.32 |

— High purity water with no NAOH addition

While a construction and assembly method has been described, the appended claims are not to be limited by such description as it will be obvious to those skilled in the art that there are other brazing and construction techniques that may be used to form the conductivity probe of this invention.

What is claimed is:

1. An electrical conductivity sensor designed to withstand high temperatures, pressures and nuclear radiation, an alumina insulator having a base region with an external attachment surface, and an integrally formed post with an external attachment surface, the post extending from the base region and having a channel extending through the post and base for conveying a conductor insulatively through the insulator;

a first metallic coating intimately adhered to the external attachment surface of the post, and a second metallic coating intimately adhered to the base external attachment surface, the first and second metallic coatings being formed to accept a braze bond;

a central electrode formed from a select metal exhibiting a coefficient of thermal expansion compatible with the alumina insulator and resistant to corrosion in a boiling water reactor, the central electrode having a concave interior surface with a third metallic coating intimately adhered thereto for accepting a braze bond, the central electrode being positioned over the external attachment surface and brazed thereto in a compressive seal;

sleeve means formed of a first select metal exhibiting a coefficient of thermal expansion compatible with the alumina insulator and resistant to corrosion in a boiling water reactor, the sleeve means having an acceptance portion with a fourth metallic coating intimately adhered thereto for accepting a braze bond, the acceptance portion being in compressive sealed brazed connection with the base external attachment surface of the insulator and insulatively separated from the central electrode, the sleeve means having a first internal channel extending along the lengthwise extent thereof;

a counter-electrode formed from a select metal resistive to corrosion in a boiling water reactor, the counter-electrode being attached with an electrically conducting bond to the sleeve means and extending over the central electrode at a fixed spaced distance, the counter-electrode containing a plurality of openings to permit a continuous exchange of fluid to fill the gap between the central electrode and the counter-electrode;

a conductor connected in electrical contact with the interior surface of the central electrode and insulatively extending therefrom through the channel in the insulator and insulatively extending through the first internal channel in the sleeve means; and positioning and signal transfer means for operatively supporting the sleeve means and conveying signals to and from the conductor and the sleeve means.

2. The electrical conductivity sensor of claim 1, wherein the alumina insulator is single crystalline alumina.

3. The electrical conductivity sensor of claim 1, wherein the central electrode is made from platinum.

4. The electrical conductivity sensor of claim 1, wherein the central electrode is made from Kovar.

5. The electrical conductivity sensor of claim 1, wherein the sleeve means is made from Kovar.

6. The electrical conductivity sensor of claim 1, wherein the counter-electrode is made from platinum.

7. The electrical conductivity sensor of claim 1, wherein the counter-electrode is made from Kovar.

8. The electrical conductivity sensor of claim 1, wherein the counter-electrode is made from a wire mesh screen.

9. The electrical conductivity sensor of claim 4, wherein the Kovar central electrode has a Platinum-black plating.

* * * * *